(12) United States Patent
Chung et al.

(10) Patent No.: US 9,421,164 B2
(45) Date of Patent: Aug. 23, 2016

(54) STIMULI RESPONSIVE ADHESIVE GEL FOR REMOVAL OF FOREIGN PARTICLES FROM SOFT TISSUE

(71) Applicant: CALIFORNIA INSTITUTE OF TECHNOLOGY, Pasadena, CA (US)

(72) Inventors: Hoyong Chung, Pasadena, CA (US); Robert H. Grubbs, South Pasadena, CA (US); Daniel M. Schwartz, San Francisco, CA (US)

(73) Assignee: California Institute of Technology, Pasadena, CA (US)

( * ) Notice: Subject to any disclaimer, the term of this patent is extended or adjusted under 35 U.S.C. 154(b) by 14 days.

(21) Appl. No.: 14/254,183

(22) Filed: Apr. 16, 2014

(65) Prior Publication Data
US 2014/0315955 A1    Oct. 23, 2014

Related U.S. Application Data

(60) Provisional application No. 61/813,566, filed on Apr. 18, 2013.

(51) Int. Cl.
*A61K 9/00* (2006.01)
*A61L 24/00* (2006.01)
*A61L 24/06* (2006.01)

(52) U.S. Cl.
CPC ........... *A61K 9/0048* (2013.01); *A61L 24/0015* (2013.01); *A61L 24/06* (2013.01); *A61L 2300/402* (2013.01)

(58) Field of Classification Search
CPC .. A61K 9/0048; A61L 24/0015; A61L 24/06; A61L 2300/402; C08L 33/26
See application file for complete search history.

(56) References Cited

U.S. PATENT DOCUMENTS

| | | | | |
|---|---|---|---|---|
| 7,732,539 B2* | 6/2010 | Shull | ................ | C08F 8/30 525/242 |
| 2004/0202625 A1* | 10/2004 | Daniloff | ................ | A61L 31/14 424/63 |
| 2005/0085791 A1* | 4/2005 | Shaw | ................ | A61L 15/44 604/506 |
| 2012/0003888 A1* | 1/2012 | Lee | ................ | A61L 24/043 442/1 |
| 2012/0156164 A1* | 6/2012 | Park | ................ | A61L 24/0015 424/78.3 |

OTHER PUBLICATIONS

Haeshin Lee, et al, Single-Molecule Mechanics of Mussel Adhesion, 103 PNAS 12999 (Aug. 29, 2006).*
Hoyong Chung & Robert Grubbs, Rapidly Cross-Linkable DOPA Containing Terpolymer Adhesives and PEG-Based Cross-Linkers for Biomedical Applications, 45 Macromolecules 9666 (2012).*
Abelson et al., "Normal Human Tear pH by Direct Measurement", Arch. Ophthalmol., 1981, 99(2), 301.
Batchelor et al., "Impact of Protein Denaturants and Stabilizers on Water Structure", J. Am. Chem. Soc., 2004, 126(7), 1958-1961.
Bowditch, "The Durability of Adhesive Joints in the Presence of Water", Int. J. Adhesion and Adhesives, 1996, 16(2), 73-79.
Catalano R.A., ed., Ocular Emergencies, WB Saunders, Philadelphia, PA, 1992, 179-196.
Chen et al., "Elastomeric Biomaterials for Tissue Engineering", Prog. Polym. Sci., 2013, 38(3-4), 584-671.
Chung et al., "Rapidly Cross-Linkable DOPA Containing Terpolymer Adhesives and PEG-Based Cross-Linkers for Bomedical Applications", Macromolecules, 2012, 45(24), 9666-9673.
Du et al., "Effects of Salt on the Lower Critical Solution Temperature of Poly (N-Isopropylacrylamide)", J. Phys. Chem. B, 2010, 114(49), 16594-16604.
Faure et al., "Catechols as Versatile Platforms in Polymer Chemistry", Prog. Polym. Sci., 2013, 38(1), 236-270.
Fujishige et al., "Phase Transition of Aqueous Solutions of Poly(N-isopropylacrylamide) and Poly(N-isopropylmethacrylamide)", J. Phys. Chem., 1989, 93(8), 3311-3313.
Furyk et al., "Effects of End Group Polarity and Molecular Weight on the Lower Critical Solution Temperature of Poly(N-isopropylacrylamide)", J Polymer Sci Part A: Polymer Chemistry, 2006, 44(4), 1492-1501.
Gil et al., "Stimuli-Responsive Polymers and Their Bioconjugates", Prog. Polym. Sci., 2004, 29(12), 1173-1222.
Lee et al., "Mussel-Inspired Adhesives and Coatings", Annu. Rev. Mater Res., 2011, 41, 99-132.
Lee et al., "Single-Molecule Mechanics of Mussel Adhesion", P. Natl. Acad. Sci USA, 2006, 103(35), 12999-13003.
Lo Nostro et al., "Hofmeister Phenomena: An Update on Ion Specificity in Biology", Chem. Rev., 2012, 112(4), 2286-2322.
Mano, "Stimuli-Responsive Polymeric Systems for Biomedical Applications", Adv. Eng. Maters., 2008, 10(6), 515-527.
Odian, Autoacceleration. In Principles of Polymerization, $4^{th}$ ed., John Wiley &Sons, Inc.: Hoboken, 2004; pp. 282-289.
Schild, "Poly(N-isopropylacrylamide): Experiment, Theory and Application", Prog. Polym. Sci., 1993, 17(2), 163-249.
Schild et al., "Microcalorimetric Detection of Lower Critical Solution Temperatures in Aqueous Polymer Solutions", J. Phys. Chem., 1990, 94(10), 4352-4356.
Sedó et al., "Catechol-Based Biomimetic Functional Materials", Advanced Materials, 2013, 25(5), 653-701.
Spector et al., "Chemical, Thermal, and Biological Ocular Exposures", Emerg. Med. Clin N. Am., 2008, 26(1), 125-36.
Wagoner, "Chemical Injuries of the Eye: Current Concepts in Pathophysiology and Therapy", Surv. Ophthalmol., 1997, 41(4), 275-313.
Waite, "Reverse Engineering of Bioadhesion in Marine Mussels", Ann. Ny. Acad. Sci., 1999, 301-309.
Waite, "Adhesion à la Moule", Integr. Comp. Biol., 2002, 42(6), 1172-1180.
Yamamoto et al., "Synthesis and Wettability Characteristics of Model Adhesive Protein Sequences Inspired by a Marine Mussel", Biomacromolecules, 2000, 1(4), 543-551.
Yu et al., "Role of L-3,4-Dihydroxyphenylalanine in Mussel Adhesive Proteins", J. Am. Chem. Soc., 1999, 121(24), 5825-5826.
Zhang et al., "Specific Ion Effects on the Water Solubility of Macromolecules: PNIPAM and the Hofmeister Series", J. Am. Chem. Soc., 2005, 127(4), 14505-14510.

* cited by examiner

*Primary Examiner* — Sean Basquill
(74) *Attorney, Agent, or Firm* — Baker & Hostetler LLP

(57) ABSTRACT

The present inventions are directed to novel aqueous compositions comprising a copolymer having water-soluble units and pendant catechols, said composition adapted for use on mammalian tissue and having a lower critical solubility temperature (LCST) of less than a physiological temperature, and their use, for example, in removing foreign particles from tissue surfaces, including ocular surfaces.

21 Claims, 10 Drawing Sheets

Poly(PEG methacrylate)
n = 2~10

N,N-diethylacrylamide
(PDEAAm)

N-vinylcaprolactam
(PVCL)

2-(dimethylamino)ethyl methacrylate
(PDMAEMA)

Poly(PEG methacrylate)
copolymer

PEO-PPO-PEO triblock copolymer

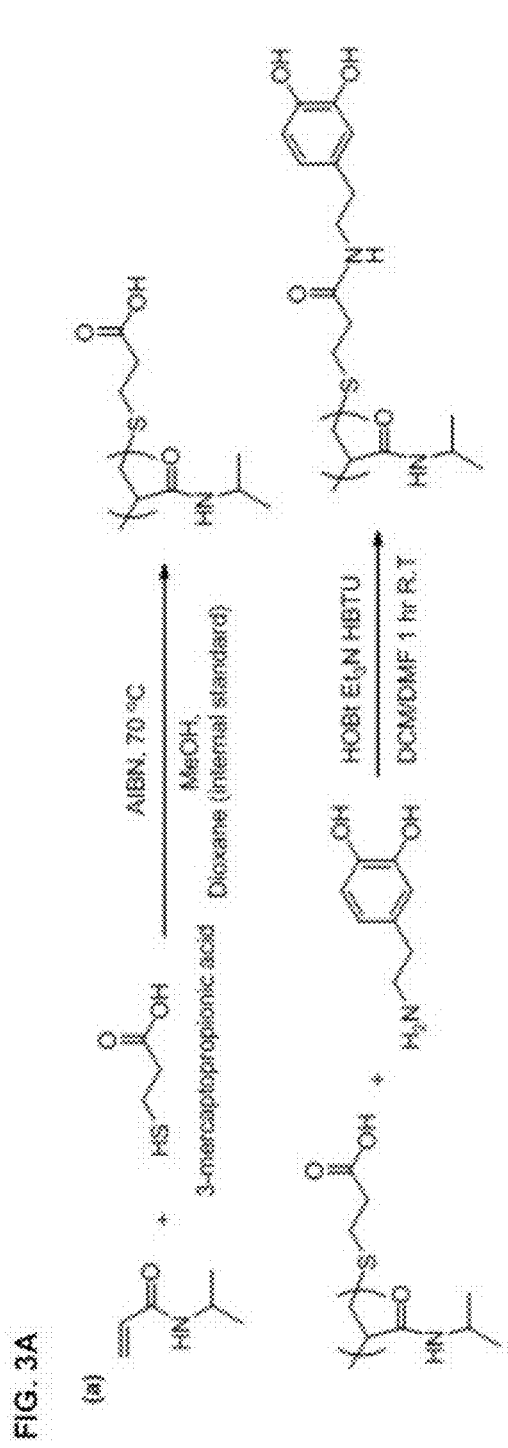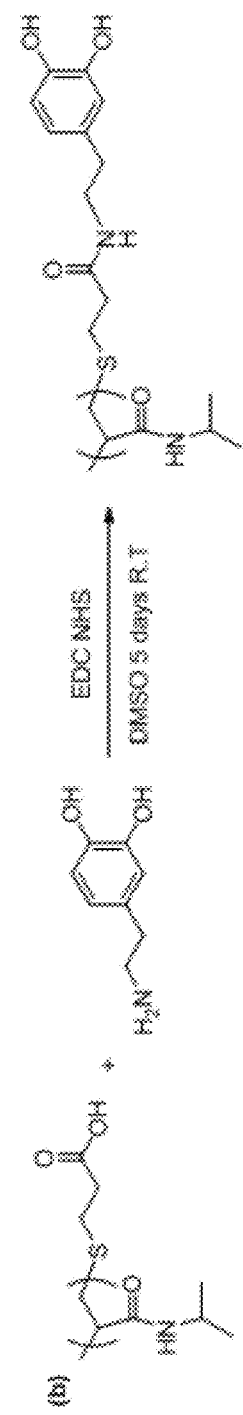
FIG. 3A
FIG. 3B

STIMULI RESPONSIVE ADHESIVE GEL FOR REMOVAL OF FOREIGN PARTICLES FROM SOFT TISSUE

CROSS REFERENCE TO RELATED APPLICATIONS

This application claims priority to U.S. application Ser. No. 61/813,566, filed Apr. 18, 2013, which is incorporated by reference herein in its entirety.

TECHNICAL FIELD

The present invention relates, at least in part, to medical adhesives and their use in treatment.

BACKGROUND

Chemical injuries to the eye are the second leading cause of work related ocular injury. Such injuries can be very serious, particularly those with alkali. These injuries can be caused by liquids, solids, aerosol, and powders. The injuries can occur at home (detergents, solvents, ammonia), industry, agriculture (fertilizers), and in construction (plaster, cement). In contrast to acid injuries that precipitate proteins, and create a penetration barrier, alkali rapidly penetrates the cornea, causing severe damage to intraocular structures. Chemical injuries can cause visual loss from damage to the ocular surface, corneal ulceration, glaucoma, and severe intraocular inflammation.

Management of chemical injuries requires immediate irrigation of the eye(s) with water or a balanced saline solution. pH is monitored before and after irrigation. Because particulate matter can lodge underneath the eyelids or the conjunctival fornix, this is of particular concern because these particles can continue to leach out toxic chemical(s) once irrigation is stopped. Therefore, the fornices and conjuctiva are swept with a cotton tip swab to remove these particles. In contrast to ocular irrigation, this technique is challenging to perform, requires topical anesthesia, and is generally reserved for physicians to complete after the patient has been transported to a medical facility. Non-leaching particulate matter (ocular foreign bodies) can lodge underneath the eyelid and may persist there in spite of copious irrigation where they cause discomfort and disruption of the ocular surface. These must often be removed carefully by medical personnel under topical anesthesia.

As an alternative to removal of ocular particulate matter by swabbing with a moist cotton tipped swab, herein we describe the use of instilled polymers that bind particulate matter, and upon solidification at body temperature, enable removal of the particles. These particle removing polymers are unique in that by virtue of being applied as a liquid, they can bind to all the irregular interstices of the ocular surface. Furthermore, they are not so strongly adhesive that they damage the ocular surface on solidification and removal from the eye. Lastly, ocular drugs (topical anesthetics, antibiotics, glaucoma medicines) can be combined with the polymer solution to allow these agents to work with instillation of the polymer solution onto the eye.

The present invention addresses some of the deficiencies in the existing art.

SUMMARY

The present inventions are directed to novel compositions and their use, for example, in removing foreign particles from eyes and mucosal membranes, and other tissue surfaces.

Certain embodiments provide aqueous compositions, each composition comprising a copolymer having water-soluble units and pendant catechols, said composition having a lower critical solubility temperature (LCST) of less than a physiological temperature of a mammalian patient. In some of these embodiments, the patient is a human, and the physiological temperature is the ocular surface of the patient. In some embodiments, the composition is formulated to be acceptable for medical use in humans.

In some embodiments, the water soluble units are derived from N,N-diethylacrylamide, N,N-dimethylacrylamide, 2-(dimethylamino)ethyl(meth)acrylamide, 2-(dimethylamino)ethyl(meth)acrylate, N-isopropylacrylamide, polyethylene glycol (PEG) (meth)acrylate (PEG having 10-1000 mw), PEO-PPO-PEO copolymers, PEO-PPO copolymers, PPO-PEO-PPO copolymers, N-vinylcaprolactam, or a mixture or copolymer thereof.

In some embodiments, the catechol is incorporated in a 3,4-dihydroxyphenyl alanine, or a 3,4-dihydroxy-L-phenyl alanine.

Certain embodiments also provide that the aqueous compositions optionally comprise salts, at least one topical anesthetic, at least one antibiotic or other medicament, at least one ophthalmic dye, or a combination thereof.

Other embodiments provide for the use of these compositions in methods of removing particles from a tissue (including an ocular surface) of a mammalian patient (including a human patient), each method comprising:

(a) applying an aqueous composition of claim 1 onto the tissue surface of the mammal, said tissue surface contaminated with at least one foreign particle, said aqueous composition being at a temperature less than the temperature of the tissue surface; and (b) waiting sufficient time for the temperature of the composition to equilibrate to the temperature of the tissue surface, optionally applying heat to the aqueous composition while on the tissue surface, such that the copolymer precipitates from the composition onto the tissue surface.

In further embodiments, the methods provide for (c) removing the precipitated copolymer and the adhered foreign particle(s) from the tissue surface.

In particular embodiments, the patient is a human.

In other embodiments, the tissue surface is the ocular surface of the patient.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

(FIG. 2A) synthesis of homo poly-NIPAM (FIG. 2B) synthesis of poly(NIPAM-co-MDOPA) (FIG. 2C) synthesis of poly(NIPAM-co-Acrylic acid-co-MDOPA) (FIG. 2D) synthesis of poly(NIPAM-co-N-phenylacrylamide)

FIG. 3A and FIG. 3B shows two schemes for functionalizing poly-NIPAM for removing particles from the eyes.

FIG. 6C, where solidified copolymer is easily removable by tweezers without remaining severe solid polymer debris.

(FIG. 7A) Eye of rabbit (FIG. 7B); Foreign particles (charcoal powder) on ocular surface (FIG. 7C); Irrigation of eye with saline to remove particles (FIG. 7D); Many remaining particles even after saline irrigation (FIG. 7E); Application of PNIPAM solution to eye (FIG. 7F); Moderate heating with hair dryer (FIG. 7G); Removal of white soft solid with tweezers (More than 95% of residual charcoal particles were removed) (FIG. 7H); Application of fluorescein solution to cornea showing no evidence of epithelial defect.

(FIG. 8E); Checking under the eye lid: particles were removed together with solidified PNIPAM.

DETAILED DESCRIPTION OF ILLUSTRATIVE EMBODIMENTS

Figure 1:
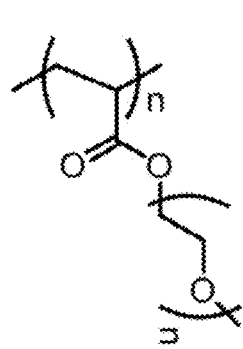
FIG. 1 provide structures of monomers and polymers useful for removal of foreign particles from eyes and other mucosal surfaces.
Figure 1:
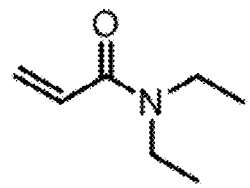
Figure 1:
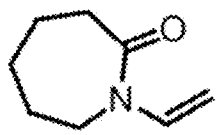
Figure 1:
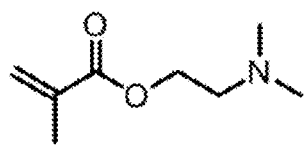
Figure 1:
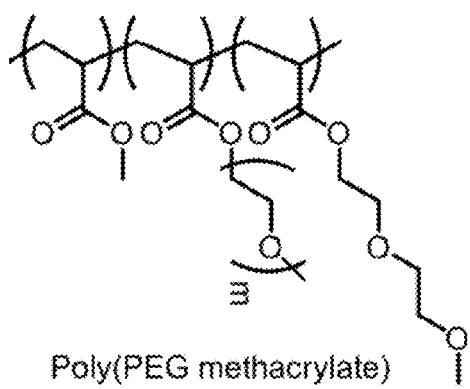
Figure 1:
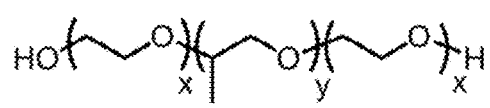

Certain polymers change physical or chemical properties by the response of stimuli, and so may be referred to as stimuli responsive polymers. Specifically, hydrogels that shows temperature-response character near human body temperature can have useful biomedical applications. The most extensively studied temperature responsive polymer in biomedical science is poly(N-isopropylacrylamide) (PNIPAM or poly-NIPAM), which demonstrates a lower critical solution temperature (LCST) at 32° C. in water. Below the LCST, PNIPAM is soluble as an extended random coil conformation in water. Above the LCST, the PNIPAM polymer chains collapse (shrinks) and showed hydrophobic nature. This temperature sensitive feature of PNIPAM can be used for drug delivery, chemo-mechanical devices, scaffolds, patches, and many other biomedical applications.

The LCST of NIPAM homopolymer is 32° C. and this temperature is useful for general application of human body. However, more precise control of LCST is needed for extensive biomedical applications because each part of human body exhibits slightly different temperatures. For instance, outer skin or externally exposed part of body may have slightly lower temperature than internally located organs. Also the temperature of externally exposed part of body can be changed according to the temperature of exposed environment. In most cases, lower LCST is required than 32° C. for exposed body parts.

The least complicated method of lowering the LCST is an addition of salt to aqueous PNIPAM solution. Other methods, such as changing molecular weight and concentration of the PNIPAM polymer hardly affects LCST. The effect of salt ions to LCST is often referred to as the specific ion effect or Hofmeister effect. In the specific ion effect, anions, cations and excluded volume effect of PNIPAM can explain the LCST decrease in salt solution. Anions can polarize a water molecule that is directly involved in hydrogen bonding with the amide. This causes destabilizing of hydrogen bonding between PNIPAM and water, and therefore it lowers the LCST. Anions can also interfere with hydrophobic hydration of PNIPAM by increasing the surface tension at the hydrophobic aqueous interface. As the salt concentration increases, the surface tension is increased at the aqueous/polymer interface. Cations have strong affinity with the oxygen of amide functionality in the PNIPAM. The cation-oxygen interaction is favored at lower temperature which can cause lowering the LCST of PNIPAM. The excluded volume effect explains the LCST changes that the solute molecules of the present salt take up space in the solution, leaving less space for the PNIPAM. Thus the PNIPAM polymer chain collapse and become hydrophobic in the presence of salt at lower temperature.

The strong wet adhesion properties of mussels is attributed to specialized amino acid, 3,4-dihydroxy-L-phenylalanine (DOPA), in their holdfast proteins. The chemical structure of DOPA can be chemically synthesized and utilized to many artificial adhesives to improve its wet adhesion in the presence of water. In general, water significantly prohibits the strength of interfacial adhesion. The interfacial physical attraction, van der Waals forces, can be displaced by water instead of either adhesive surface or adherend surface. Therefore, adhesive and adherend loses its direct contact due to existence of water. Also water can infiltrate and plasticize adhesives and/or adherends and consequently it weaken the interfacial adhesion properties. Adhesives and adherends undergo chemical degradation such as hydrolysis that may be induced by water.

DOPA functionality in polymer can overcome those listed issues that caused by water and eventually helped to increase wet adhesion property. The adhesion mechanisms of DOPA containing polymers to universal types of adherend surface were scientifically explained by a few different theories. Catechol groups in DOPA functionality and organic surfaces can form covalent bonds via Michael addition reaction according to some research. Catechol groups in DOPA can also form coordination bonds to metallic surfaces. The catechol group can covalently crosslink via redox reaction between catechol containing polymer chains and proteins. This crosslink enhance cohesive strength of overall adhesive after interfacial adhesion is occurred. Some have suggested that the polar surface typically represented as a glass surface, can have strong interaction to hydrophilic side chains of hydroxyl and amino group in DOPA-containing polymers. Non-polar surface, high density polyethylene, can have high interfacial attractions with hydrophobic portion of DOPA-containing polymers such as alkyl groups.[20] Using the extraordinary wet adhesion properties of DOPA containing polymer, many applications have been reported including biomedical field. The DOPA functionality's wet adhesion property is introduced to NIPAM-based temperature sensitive polymer to effectively capture the foreign particles on eyes.

The present invention relates to compositions comprising polymers or copolymers, said polymers or copolymers comprising pendant catechol groups, for example derived from 3,4-dihydroxyphenylalanine, and said compositions having LCST below physiological temperatures, especially below ocular temperatures of mammals and humans. The polymers preferably provide sufficient adhesion to adhere non-tissue particulates, but not so much as to cause tissue damage when applied and removed from said tissue, especially ocular surfaces. This disclosure teaches methods for optimizing LCST, adhesion, and mechanical and viscoelastic properties by choice of appropriate polymers or copolymers and added salt and other additives.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to both compositions and methods of making and using said compositions. That is, where the disclosure describes and/or claims a feature or embodiment associated with a composition, it is appreciated that such a description and/or claim is intended to extend these features or embodiment to embodiments encompassing the method of making or using a composition, and vice versa.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled the relevant art. However, so as to avoid misunderstanding, the meanings of certain terms will be specifically defined or clarified.

The present invention includes embodiments related to aqueous compositions, each aqueous composition comprising a copolymer comprising water-soluble units and pendant catechols, the composition having a lower critical solubility temperature (LCST) of less than a temperature harmful to mammalian (independently including human) tissue, preferably less than a physiological temperature of a mammalian (independently including human) patient.

As used herein, the term "mammalian tissue" carries its normal connotation, including epithelial tissue. In particularly attractive embodiments, the term refers to mucosal and soft tissue and ocular surfaces, especially ocular surfaces. Mammalian tissue includes human tissue, again especially human ocular surfaces.

As used herein, unless otherwise specified, the term "lower critical solubility temperature" or "LCST" refers to the temperature at which the copolymer substantially precipitates from the composition to form a continuous solid copolymer phase, at the polymer concentration used in the composition. Below this temperature, the copolymer is soluble, miscible, or fully dispersed in the aqueous composition at the concentration employed. In preferred embodiments, the copolymer is fully soluble or miscible below the LCST. Unless otherwise specified, the term "substantially precipitates" refers to the condition in which the polymer precipitates in an amount sufficient for the purposes described herein; for example, to provide a solid coating layer on the tissue surface (e.g., ocular surface) having the mechanical and viscoelastic characteristics suitable for handling. In preferred embodiments, these characteristics allow for the solid copolymer to be removed from the tissue (ocular) surface as a single piece. In certain independent embodiments, this amounts to at least 10 wt %, 20 wt %, 30 wt %, 40 wt %, 50 wt %, 60 wt %, 70 wt %, 80 wt %, 90 wt %, 95 wt %, or practically all of the copolymer originally contained in the mixture at temperatures below the LCST.

Alternatively, in some embodiments, the solid copolymer may be removed by cooling the copolymer in the presence of the aqueous composition, so as to re-dissolve the copolymer in that composition, after which the composition may be flushed away with water or another medically acceptable aqueous solution.

The temperature defining the LCST should be one compatible with mammalian or human tissue. In its broadest context, this includes temperatures less than those harmful to the tissue, but preferably temperature defining the LCST is comparable to the physiological temperature associated with the specific tissue to which the composition is to be or is being applied, noting that different tissues can exhibit different physiological temperatures. It is envisioned that the solubilized or miscible compositions are to be applied to these various tissues, especially to the ocular surfaces of human eyes, at a temperature below the normal tissue or ocular temperature and below the LCST of the compositions. On equilibrating to the temperature or the ocular surface, the composition passes through the LCST of the composition, wherein the copolymer precipitates onto the eye as a continuous polymer film. In some cases, it may be useful to apply additional heat (i.e., above the inherent heat of the tissue or ocular surface) to the composition, so as to encourage complete or additional precipitation of the copolymer on the surface. In specific embodiments, the lower critical solubility temperature (LCST) of the composition is in a range of about 15° C. to about 35° C., preferably in a range of from about 30° C. to about 34° C. For compositions intended for ocular surfaces, the lower critical solubility temperature (LCST) of the composition can be less than about 32° C. In other embodiments, where the application of heat may be warranted, compositions exhibiting higher LCSTs may be suitable, for example up to about 40° C. or about 45° C., for short periods of time. Again, higher temperatures may be suitable, provided such temperatures are not harmful to the tissues to which the compositions are to be administered.

The term "copolymer" is used to reflect that the polymer comprises water soluble units and units comprising catechol functionality, and not necessarily the means of their preparation. The term "unit" is used to describe a repeating group within a copolymer backbone, such as derived from a related monomer or oligomer.

These copolymers may include naturally derived materials, but are generally considered synthetic materials, in the sense that, as a whole, they are not found in nature or can merely be extracted from natural products (e.g., are not merely peptide copolymers). While the copolymers are not necessarily limited by their method of preparation, they may be prepared by any number of conventional synthetic methods, including free radical polymerization, ring opening metathesis polymerization (ROMP), atom transfer radical polymerization (ATRP), nitroxide mediate polymerization (NMP), or reverse addition-fragmentation chain transfer polymerization (RAFT) of the respective monomers. The resulting copolymers may have any one of an array of architectures, including linear, comb shape graft (or brush) or branched multiarm architectures, or combinations thereof.

The term "water-soluble units" refers to those units which contain at least one type of hydrophilic moiety. Unless otherwise indicated, the term "water-soluble units" refers to those units which, if formed into a homopolymer of comparable Mw of the copolymer, would dissolve in water at room temperature. Other specific embodiments provide water-soluble units which include those where at least about 50 wt %, at least about 75 wt %, at least about 85 wt %, at least about 95 wt %, at least about 98 wt %, as well as when all of the corresponding homopolymer would dissolve in water at room temperature, particularly at temperatures below the LCST. Such degree of dissolution may be shown by light scattering (including Rayleigh scattering or turbidity) or transmission techniques, such as are known in the art.

Certain additional embodiments also provide that the "water-soluble units" may be defined in terms of units having at least one pendant hydroxy or ionizable groups, including, e.g., carboxylic acids, amines (including quaternary amines), betaine, sulfate, or phosphate groups, and/or oligomers or polymers of ethylene glycol (PEG), polysaccharides, or cellulosic backbone linkages or pendants. Such water-soluble units may be derived from monomers capable of providing water-soluble vinyl polymers, water-soluble poly(meth)acrylates, water-soluble polyamides, water-soluble polyesters, water-soluble polyurethanes, xanthan gums, sodium alginates, galactomannans, carageenan, gum arabic, cellulose and its derivatives, such as hydroxyethyl cellulose and hydroxypropyl cellulose, starch and its derivatives, guar and its derivatives, proteins and their derivatives, water-soluble poly(vinyl alcohol), water-soluble poly (vinyl amine), water-soluble poly(ethylene imine), water-soluble amine/epihalohydrin polyamines, water-soluble vinyl pyrrolidone, water-soluble poly(meth)acryloyloxytetraalkyl ammonium salts (e.g., halides), or mixtures thereof.

In other exemplary, non-limiting example, water-soluble units may be derived from monomers or oligomers of 2-aminoethyl methacrylate, N-(3-aminopropyl)-(meth)acrylate, carboxybetaine, citraconic acid, N,N-diethylacrylamide, N,N-dimethylacrylamide, 2-(dimethylamino)ethyl(meth) acrylamide, 2-(dimethylamino)ethyl(meth)acrylate, ethylene glycol dimethacrylate, 2-hydroxyethylmethacrylate, 2-hydroxyethylacrylate, N-isopropylacrylamide, itaconic acid, (meth)acrylamide, (meth)acrylic acid, polyethylene glycol (PEG) (meth)acrylate (PEG having 10-1000 MW), PEO-PPO-PEO copolymers, PEO-PPO copolymers, PPO-PEO-PPO copolymers, N-vinylcaprolactam, vinyl alcohol, N-vinyl pyrrolidone, or a mixture or copolymer thereof. Particularly attractive embodiments include those where the water-soluble units are derived from N,N-diethylacrylamide, N,N-dimethylacrylamide, 2-(dimethylamino)ethyl (meth) acrylamide, 2-(dimethylamino)ethyl(meth)acrylate, N-isopropylacrylamide, polyethylene glycol (PEG) (meth)acrylate (PEG having 10-1000 MW), PEO-PPO-PEO copolymers, PEO-PPO copolymers, PPO-PEO-PPO copolymers, N-vinylcaprolactam, or a mixture or copolymer thereof.

For the sake of absolute clarity, as used herein, the convention of using the parenthetical "(meth)," as in "(meth)acrylamide" and (meth)acrylic acid is intended to connote independent embodiments of acrylamide methacrylamide and acrylic acid methacrylic acid, respectively, or derivatives thereof.

In these copolymers, the water-soluble units of these compositions may be arranged in mixed block segments with non-water-soluble units within the copolymers (e.g., PEO-PPO-PEO or PPO-PEO-PPO copolymers). Note that the term "segment" is intended to connote a portion of the copolymer composed either entirely of a particular type of unit or of sufficient amounts of such units as to engender that portion of the copolymer with the character of the predominant unit. Preferably the various units are each randomly distributed throughout the copolymer. The term "randomly distributed" is intended to connote a distribution throughout the polymer reflecting the statistical composition of the units. It is preferred, but not required, that each of the units is a separate derivative or analog of a common monomer base, for example, of a (meth)acrylic acid.

Where each aqueous composition is described as comprising a copolymer comprising water-soluble units and pendant catechols, the pendant catechols may be attached to the copolymer either directly or via linking groups. 3,4-dihydroxyphenyl alanine is an effective source of catechol groups in this application, including 3,4-dihydroxy-L-phenyl alanine. The use of 3,4-dihydroxyphenyl alanine provides a convenient source of these catechol groups. These catechol-containing groups may be randomly distributed throughout the copolymer chain, may be arranged in at least one block polymer segment in the copolymer, or may be limited to the ends of the copolymer chains.

Given the ability of the catechol moieties to attach to tissue, including ocular surfaces, it is desirable to keep their relative concentrations low within the copolymer. In certain independent embodiments, the concentration of pendant catechols, for example as 3,4-dihydroxyphenyl alanine, within the copolymer in a range of about 0.01 to about 10 mol %, based on the total molar composition of the copolymer. In other exemplary embodiments, the concentration of these catechol moieties, for example as 3,4-dihydroxyphenyl alanine, may be in a range from about 0.01 to about 0.1 mol %, from about 0.1 to about 1 mol %, from about 1 to about 2 mol %, from about 2 to about 3 mol %, from about 3 to about 4 mol %, from about 4 to about 5 mol %, from about 5 to about 6 mol %, from about 6 to about 10 mol %, or a combination thereof. The specific concentration depends on the nature of the water soluble units in the copolymer backbone. For example, the range of from about 3 to about 6 mol %, or about 2.5 mol % seems to work well when the polymer comprises poly(N-isopropylacrylamide) (PNIPAM).

Again, the average molecular weight of the copolymers is less important than the ability to exhibit the LCST parameters described herein. Having said this, the copolymers may also be characterized by their average molecular weight. Unless otherwise specifically stated, the term "average molecular weight," as used herein, refers to number averaged molecular weight, $M_n$. In certain independent embodiments, the number-averaged molecular weight ($M_n$) of the non-crosslinked copolymer will be at least about 2000 daltons, at least about 5000 daltons, at least about 10,000 daltons, at least about 20,000 daltons, or at least 25,000 or 50,000 daltons. In related independent embodiments, the number-average molecular weight of the copolymer(s) will be less than about 500,000, less than about 300,000, less than about 250,000, less than about 100,000, or less than about 50,000 daltons. In other embodiments, in the inventive compositions, the copolymer has a numbered average molecular weight, $M_n$, in a range of from about 10,000 to about 500,000 g/mol, preferably in a range of 40,000 to about 300,000 g/mol. Again, the specific nature of the water-soluble groups and concentrations, and the other components in the composition (e.g., salt) effect the specific preferred molecular weight ranges. For example, when the water soluble portion of the copolymer comprises essentially poly(N-isopropylacrylamide) (PNIPAM), preferred number averaged molecular weights are in a range of from about 100,000 to about 200,000 g/mol, and more preferably about 160,000 g/mol.

The $M_n$ of the copolymers may be determined by conventional GPC (gel permeation chromatography), by viscometry of dilute polymer solutions, by diffusion ordered NMR spectroscopy (DOSY) using diffusion coefficients of polymers in solution, or by Matrix-Assisted Laser Desorption/Ionization-Time of Light Mass Spectrometry (MALDI-TOF MS). MALDI-TOF MS is perhaps the most direct method for determining Mw and Mw distributions in a polymer sample, and is preferred on this basis. For those systems for which MALDI-TOF MS is not appropriate, GPC methods (e.g., using DMF or water eluents) are also especially useful. The specific conditions of each test depend on the specific nature of the copolymer, and the skilled artisan would be capable of defining and measuring to such conditions.

The operability of the compositions and the methods described herein also depend on the initial concentrations of the copolymer in the compositions; i.e., at temperatures below the LCST. In certain exemplary embodiments, the copolymer concentration may be in a range of from about 10 mg/mL to about 500 mg/mL of total composition, or from about 50 mg/mL to about 250 mg/mL of total composition. In the compositions described in the Examples, these latter ranges well-describe preferred embodiments.

As used herein, the term "aqueous" carries its conventional meaning, referring to a composition in which water is the predominant phase or solvent. However, the compositions may also contain other materials, for example, including physiological fluids such as serum, plasma, blood, tears, mucosal fluid).

The specific LCST exhibited by a polymer or copolymer depends not only on the polymer or copolymer itself or the temperature of the composition, but also upon other additives which may be included in the composition, particularly salts. Indeed the presence of salts or other additives is a convenient way of tuning the LCST for a given polymer or copolymer system (see, e.g. Example 6). Solutions containing sodium chloride (saline) are often used for this purpose, though other medically acceptable buffers (e.g., phosphate buffers) or rheology modifiers may also be employed. The LCST of certain polymers may be greatly effects by only small amounts of electrolytes, for example, sodium chloride, again depending on the particular polymer. But in certain embodiments, sodium chloride present in a range of from about 0.1 to about 10 wt %, relative to the weight of the total composition have been shown to be effective. In other preferred embodiments, the sodium chloride or other medically acceptable salts, may be present in concentrations in a range of from about 0.1 to about 0.2 wt %, from about 0.2 to about 0.5 wt %, from about 0.5 to about 1 wt %, from about 1 to about 2 wt %, from about 2 to about 3 wt %, from about 3 to about 4 wt %, from about 4 to about 5 wt %, from about 5 to about 7 wt %, from about 7 to about 10 wt %, or a combination thereof. Again, in the poly(N-isopropylacrylamide) (PNIPAM)-3,4-dihydroxyphenylalanine system described in the Examples, a preferred range appears to be from about 1 to about 3.5 wt %, or about 2.5 wt %.

Additionally, especially when the compositions are contemplated for use in a patient's eyes, or other sensitive body regions, the composition may further comprise one or more topical anesthetics, such as Proparacaine, Tetracaine, Lidocaine, or Bupivacaine. Compositions for use in a patient's eyes may also contain an ophthalmic dye for interrogating the eye after treatment with the composition.

The composition may further comprise one or more antibiotic, antiviral, or antifungal material, or other medicament, for example for the treatment of glaucoma or uveitis. A particular choice of such a material depends on the contemplated use of the compositions, and one skilled in the art may be able to select appropriate materials in this regard.

The compositions may be formulated to be applied as liquid drops, or as a dip coating, or as a spray or aerosol. The viscosity of the compositions should be such that the kinetics of the copolymer deposition are sufficiently fast as to be practical in their intended application.

The compositions of the present invention may be, but are not necessarily, directed to mammalian use, including for use on humans, and in certain embodiments the compositions and methods are adapted so as to be acceptable for these purposes. While not necessarily required for all applications, in such cases where the compositions are contemplated for use, or are actually used, with mammals, including humans, it is at least highly preferred that the compositions be made of materials and be of sufficient character as to be acceptable for medical applications (in some cases for use as implantable materials); e.g., as appropriately recognized acceptable by the U.S. Food and Drug Administration or analogous other regulatory agency in other countries.

Taken together, one specific embodiment would include an aqueous composition comprising a copolymer comprising water-soluble units and pendant 3,4-dihydroxyphenyl alanine, the composition having a lower critical solubility temperature (LCST) of less than 32° C.; wherein the 3,4-dihydroxyphenyl alanine is present in the copolymer in a range of about 3 to about 6 mol %, based on the total molar composition of the copolymer;

the water-soluble units derived from N,N-diethylacrylamide, N,N-dimethylacrylamide, 2-(dimethylamino) ethyl(meth)acrylamide, 2-(dimethylamino)ethyl(meth) acrylate, N-isopropylacrylamide, polyethylene glycol (PEG) (meth)acrylate (PEG having 10-1000 MW), PEO-PPO-PEO copolymers, PEO-PPO copolymers, PPO-PEO-PPO copolymers, N-vinylcaprolactam, or a mixture or copolymer thereof;

the copolymer having a number average, $M_n$, molecular weight in a range of from about 100,000 to about 200,000 g/mol and being present in the composition in a range of about 1 to about 3.5 wt %, relative to the weight of the total composition;

the composition comprises sodium chloride in a concentration range of about 1 wt % to about 5 wt %, relative to the weight of the composition;

the composition optionally comprises an anesthetic;

the composition optionally comprises an antibiotic;

the composition optionally comprises medicament for the treatment of glaucoma or uveitis; and the composition optionally comprises an ophthalmic dye;

the composition being acceptable for human use.

To this point, the disclosure has focused on compositions, but it should also be appreciated that some of the inventions also are directed to methods of using these compositions. For example, certain embodiments provide methods for removing particles from a tissue of a mammalian patient, especially from an eye of a mammalian patient, each method comprising:

(a) applying at least one of the aqueous compositions described herein onto the tissue (including especially a mucosal or an ocular surface) of the mammal, said tissue surface contaminated with at least one foreign particle, having a lower critical solubility temperature (LCST) less than and being at a temperature less than the temperature of the tissue surface; and (b) waiting sufficient time for the temperature of the composition to equilibrate to the temperature of the tissue surface, and optionally applying heat to the aqueous composition while on the tissue surface, such that the copolymer precipitates from the composition onto the tissue surface.

The method may further comprise (c) removing the precipitated copolymer and the adhered foreign particle(s) from the tissue surface.

While it is envisioned that the deposited polymer will ultimately be removed to remove the adhered foreign body, it need not be removed by the same person who applied the composition. For example, the application of the composition and deposition of the polymer may be done to prevent movement of the foreign body/bodies across the surface of the tissue while transporting the patient to more sophisticated medical facilities. In the case of an ocular surface, for example, this could prevent movement of particulate matter causing scoring or tearing of the cornea.

So as to be clear as to the particular utility of the methods to removing foreign particles from the eye of a mammalian patient, certain additional embodiments provide methods for removing particles from an eye of a mammal, each method comprising:

(a) applying at least one of the aqueous compositions described herein onto the ocular surface (i.e., into the eye) of the mammal, said ocular surface contaminated with at least one foreign particle, having a lower critical solubility temperature (LCST) less than and being at a temperature less than the temperature of the ocular surface; and (b) waiting sufficient time for the temperature of the composition to equilibrate to the temperature of the ocular surface, and optionally applying heat to the aqueous composition while on the ocular surface, such that the copolymer precipitates from the composition onto the ocular surface.

The method may further comprise (c) removing the precipitated copolymer and the adhered foreign particle(s) from the ocular surface.

In certain embodiments, the mammal or mammalian patient is a human or human patient. In these methods of removing particles from an eye of a human patient, each method comprising:

(a) applying at least one of the aqueous compositions described herein adapted for use with humans into the eye, onto the ocular surface, of a human patient, said tissue surface contaminated with at least one foreign particle, said aqueous composition having a lower critical solubility temperature (LCST) less than and being at a temperature less than the temperature of the eye, ocular surface, or both; and (b) waiting sufficient time for the temperature of the composition to equilibrate to the temperature of the eye, ocular surface, or both, and optionally applying heat to the aqueous composition while on the ocular surface, such that the copolymer precipitates from the composition onto the ocular surface.

The method may further comprise (c) removing the precipitated copolymer and the adhered foreign particle(s) from the eye or ocular surface.

As used herein, the term "for sufficient time" is intended to connote the temporal conditions for the desired precipitation to occur, and the polymer to attach to the foreign particulates which the method is targeting. Again, it may be useful, in some cases, to apply heat to the compositions to either accelerate or effect the deposition of the solid polymer on the tissue or ocular surface.

While the methods are described in terms of mammalian or human tissues (including soft tissues, eyes/ocular surfaces), the methods may also be applied to other biological or non-biological materials. Further, the methods may be applied mammalian or human patients or tissues that are living or not (the latter as may exist, for example, in a forensic setting).

The compositions of the present invention may also be used offer protection to damaged or compromised tissue surfaces, for example ocular surface, for example after surgery, even when the soft tissue, membrane, or ocular surface does not contain foreign particle contaminants. The compositions may also be used as a temporary delivery system for medicaments to the treated area. In some embodiments, then, application of one or more of the compositions as described herein may be used to provide a temporary eye patch, either before or after medical treatment of the affected area.

The following listing of embodiments in intended to complement, rather than displace or supersede, the previous descriptions.

Embodiment 1

An aqueous composition comprising a copolymer comprising water-soluble units and pendant catechols, the composition having a lower critical solubility temperature (LCST) of less than a physiological temperature of a mammalian patient.

Embodiment 2

The composition of Embodiment 1, having a lower critical solubility temperature (LCST) of less than 32° C., for example in a range of from about 15° C. to about 32° C.

Embodiment 3

The composition of Embodiment 1 or 2, the water-soluble units being derived from 2-aminoethyl methacrylate, N-(3-aminopropyl)-(meth)acrylate, carboxybetaine, citraconic acid, N,N-diethylacrylamide, N,N-dimethylacrylamide, 2-(dimethylamino)ethyl(meth)acrylamide, 2-(dimethylamino)ethyl(meth)acrylate, ethylene glycol dimethacrylate, 2-hydroxyethylmethacrylate, 2-hydroxyethylacrylate, N-isopropylacrylamide, itaconic acid, (meth)acrylamide, (meth)acrylic acid, polyethylene glycol (PEG) (meth)acrylate (PEG having 10-1000 MW), PEO-PPO-PEO copolymers, PEO-PPO copolymers, PPO-PEO-PPO copolymers, N-vinylcaprolactam, vinyl alcohol, N-vinyl pyrrolidone, or a mixture or copolymer thereof.

Embodiment 4

The composition of any one of Embodiments 1 to 3, the water-soluble units being derived from N,N-diethylacrylamide, N,N-dimethylacrylamide, 2-(dimethylamino)ethyl (meth)acrylamide, 2-(dimethylamino)ethyl(meth)acrylate, N-isopropylacrylamide, polyethylene glycol (PEG) (meth) acrylate (PEG having 10-1000 MW), PEO-PPO-PEO copolymers, PEO-PPO copolymers, PPO-PEO-PPO copolymers, N-vinylcaprolactam, or a mixture or copolymer thereof.

Embodiment 5

The composition of any one of Embodiments 1 to 4, the catechol being incorporated in 3,4-dihydroxyphenyl alanine.

Embodiment 6

The composition of any one of Embodiments 1 to 5, the catechol being incorporated in 3,4-dihydroxy-L-phenyl alanine.

Embodiment 7

The composition of Embodiment 5 or 6, the 3,4-dihydroxyphenyl alanine being present in the copolymer in a range of about 0.1 to about 10 mol %, based on the total molar composition of the copolymer, preferably in a range of about 3 to about 6 mol %.

Embodiment 8

The composition of any one of Embodiments 1 to 7, the copolymer having an $M_n$ molecular weight in a range of from about 40,000 to about 300,000 g/mol, preferable in a range of about 100,000 to about 200,000 g/mol, more preferably about 160,000 g/mol.

Embodiment 9

The composition of any one of Embodiments 1 to 8, having a copolymer concentration in a range of about 50 mg/mL to about 250 mg/mL of total composition.

Embodiment 10

The composition of any one of Embodiments 1 to 9, the catechol or 3,4-dihydroxy-L-phenyl alanine being arranged in at least one block polymer segment in the copolymer.

Embodiment 11

The composition of any one of Embodiments 1 to 10, the catechol or 3,4-dihydroxy-L-phenyl alanine being randomly distributed throughout the copolymer.

Embodiment 12

The composition of any one of Embodiments 1 to 11, the copolymer having been prepared by free radical polymerization, ring opening metathesis polymerization (ROMP), atom transfer radical polymerization (ATRP), nitroxide mediate polymerization (NMP), or reverse addition-fragmentation chain transfer polymerization (RAFT) of the respective monomers.

Embodiment 13

The composition of any one of Embodiments 1 to 12, further comprising sodium chloride, preferably at a concentration in a range of about 0.1 to about 10 wt %, relative to the weight of the total composition, more preferably in a range of about 1 to about 3.5 wt %.

Embodiment 14

The composition of any one of Embodiments 1 to 13, further comprising a topical anesthetic.

Embodiment 15

The composition of any one of Embodiments 1 to 14, further comprising an antibiotic.

Embodiment 16

The composition of any one of Embodiments 1 to 15, further comprising an ophthalmic dye Embodiment 17

The composition of any one of Embodiments 1 to 16, the composition being acceptable for human use.

Embodiment 18

The composition of any one of Embodiments 1 to 17:
the composition having a lower critical solubility temperature (LCST) of less than 32° C.;
the catechol incorporated in 3,4-dihydroxyphenyl alanine and being present in the copolymer in a range of about 3 to about 6 mol %%, based on the total molar composition of the copolymer;
the water-soluble units derived from N,N-diethylacrylamide, N,N-dimethylacrylamide, 2-(dimethylamino)

ethyl(meth)acrylamide, 2-(dimethylamino)ethyl(meth)acrylate, N-isopropylacrylamide, polyethylene glycol (PEG) (meth)acrylate (PEG having 10-1000 MW), PEO-PPO-PEO copolymers, PEO-PPO copolymers, PPO-PEO-PPO copolymers, N-vinylcaprolactam, or a mixture or copolymer thereof;

the copolymer having a number average, $M_n$, molecular weight in a range of from about 100,000 to about 200,000 g/mol and being present in the composition in a range of about 1 to about 3.5 wt %, relative to the weight of the total composition;

the composition comprising sodium chloride in a concentration range of about 1 wt % to about 5 wt %, relative to the weight of the composition;

the composition optionally comprising an anesthetic;

the composition optionally comprising an antibiotic;

the composition optionally comprises medicament for the treatment of glaucoma or uveitis;

the composition optionally comprising an ophthalmic dye; and the composition being acceptable for human use.

Embodiment 19

A method of removing particles from a tissue surface (including an ocular surface) of a mammalian patient (including a human patient), said method comprising:
(a) applying an aqueous composition of any one of Embodiments 1 to 18 onto the tissue surface of the patient, said tissue surface contaminated with at least one foreign particle, said aqueous composition having a lower critical solubility temperature (LCST) less than and being at a temperature less than the temperature of the tissue surface; and
(b) waiting sufficient time for the temperature of the composition to equilibrate to the temperature of the tissue surface, optionally applying heat to the aqueous composition while on the tissue surface, such that the copolymer precipitates from the composition onto the tissue surface.

Embodiment 20

The method of Embodiment 19 further comprising (c) removing the precipitated copolymer and the adhered foreign particle(s) from the tissue surface.

Embodiment 21

A method of removing particles from an eye of a human patient, said method comprising:
(a) applying an aqueous composition of any one of Embodiments 1 to 18 onto the ocular surface of a human patient, said ocular surface contaminated with at least one foreign particle, said aqueous composition having a lower critical solubility temperature (LCST) less than and being at a temperature less than the temperature of the ocular surface; and
(b) waiting sufficient time for the temperature of the composition to equilibrate to the temperature of the eye, optionally applying heat to the aqueous composition while on the eye of the patient, such that the copolymer precipitates from the composition onto the ocular surface.

Embodiment 22

The method of Embodiment 20 further comprising (c) removing the precipitated copolymer and the adhered foreign particle(s) from the ocular surface.

Embodiment 23

A method of protecting an eye of a human patient, said method comprising:
(a) applying an aqueous composition of any one of Embodiments 1 to 18 onto the ocular surface of a human patient, said aqueous composition having a lower critical solubility temperature (LCST) less than and being at a temperature less than the temperature of the ocular surface; and
(b) waiting sufficient time for the temperature of the composition to equilibrate to the temperature of the eye, optionally applying heat to the aqueous composition while on the eye of the patient, such that the copolymer precipitates from the composition onto the ocular surface.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

Example 1

Temperature Sensitive Polymers

The most common temperature sensitive polymer that has LCST behavior is PNIPAM (FIG. 2). In this study, homopolymer of NIPAM and various copolymers of NIPAM were prepared as shown in FIG. 2. The more detail PNIPAM preparation and application will be discussed in the next section. FIG. 1 shows temperature sensitive polymers that can be used for removal of foreign particles from the eyes. All of them reveal LCST behavior by the temperature. Poly(PEG methacrylate), poly(N,N-diethylacrylamide), poly(N-vinlycaprolactam), poly[2-(dimethylamino)ethyl methacrylate], poly(PEG methacrylate) copolymer, and PEO-PPO-PEO triblock copolymer can be used to remove foreign fine particles from the eyes. Aqueous solutions of polymers that listed in FIG. 1 are liquid state at room temperature but the solution turns solid at human body temperature. The liquid state has much higher mobility than solid, the polymer liquid solution can have very high contacting area with fine particles on the eyes. As the polymer solution change its state to solid, the slight decrease of overall volume can make the polymer solid grip the all fine particles on the eyes. After the solidification, the solid polymer film and foreign particles can be removed together very easily. In order to satisfy the particle removal principle, LCST behavior of polymer aqueous solution is essential. The listed polymers and monomers for the polymer can be used for this purposes.

Example 2

Synthesis of NIPAM Homopolymer and Copolymers

Figure 2A:
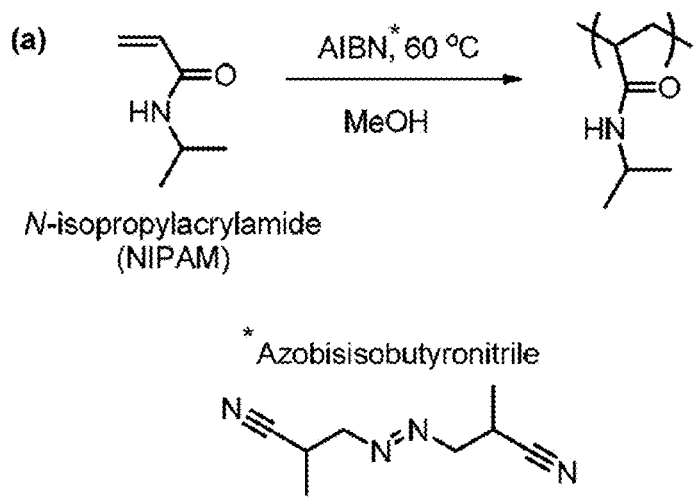
FIGS. 2A-D shows the schematics of syntheses of various NIPAM-based polymers.
Figure 2B:
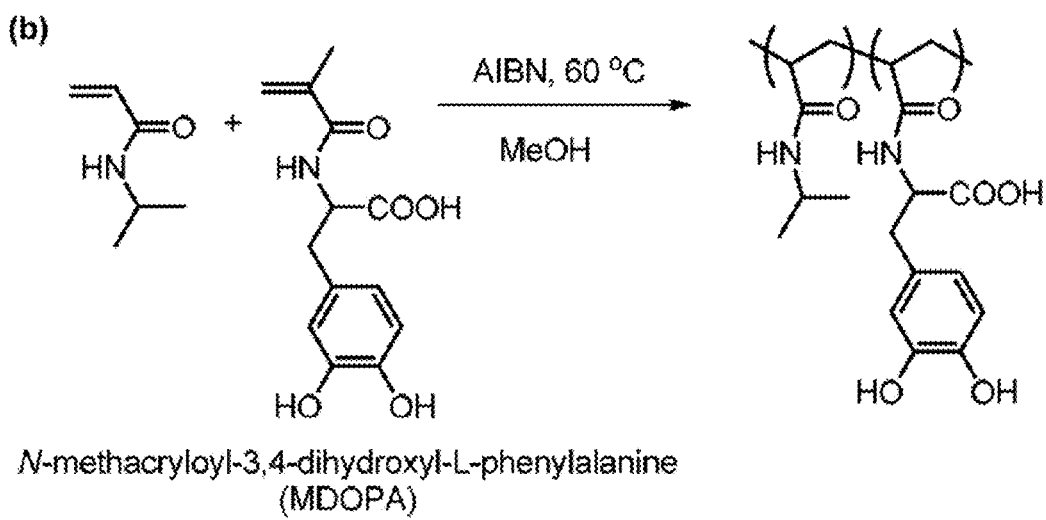
Figure 2C:
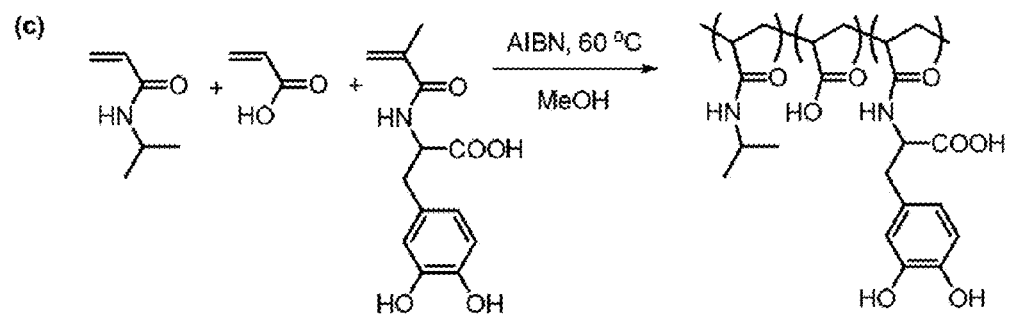
Figure 2D:
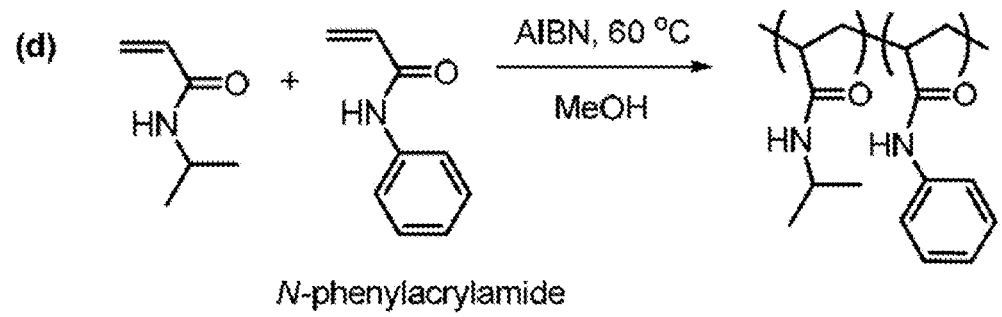

Four different NIPAM containing homo/copolymers were synthesized as shown in FIG. 2A-D. FIG. 2A represents the AIBN initiated homopolymerization of NIPAM in methanol. Two different molecular weight of PNIPAM were synthesized to compare particle capturing capability, adhesion property toward particles, with different molecular weight. FIG. 2B shows the synthetic scheme for the copolymer of NIPAM and MDOPA. DOPA functionality offered strong wet adhesion property. MDOPA was copolymerized with NIPAM but its contents were small, 5 mole % to avoid damage to the ocular surface related to excessive adhesion. FIG. 2C shows terpolymer of NIPAM, acrylic acid and MDOPA. In this terpolymer, acrylic acid was added to prepare a dual stimuli responsive polymer. Acrylic acid segment in the polymer was soluble in basic environment but insoluble under acidic environment because of protonated carboxylic acids. The acrylic acid-containing terpolymer was not pursued after a few initial experiments. This is because pure water or sodium chloride (NaCl) solution has pH about 5.5 but pH of the ocular surface is more basic (7.0-7.3). Copolymer of NIPAM and N-phenylacrylamide is shown in FIG. 2D. The N-phenylacrylamide was more hydrophobic than NIPAM due to phenyl group in the monomer structure. A small addition of hydrophobic N-phenylacrylamide to NIPAM polymer can drop the LCST of copolymer lower than homo NIPAM polymer. However, a precise control of N-phenylacrylamide in the copolymer was not easy. Even 1 mole % of N-phenylacrylamide was too high of a concentration, and the resultant copolymer was not soluble in water. It has been revealed that addition of salt is the most convenient and precise way to drop LCST of NIPAM containing polymer. This effect is specific ion effect, or Hofmeister effect.

Example 3

End Functionalization of PNIPAM

PNIPAM can also be modified to have slightly enhanced adhesion properties by using functionality catechol group. If the adhesive character of the polymer is too strong, it can hurt the cornea when the solidified polymer is removed from the eyes, but optimized adhesion can grasp the foreign particles from the eyes better. For this purposes, FIG. 2 showed copolymerization to introduce catechol groups to the PNIPAM. In FIG. 3, catechol group is located at terminals of PNIPAM polymer chains. Carboxylic acid functionalized PNIAPM can be prepared by radical polymerization with chain transfer agents. The chain transfer agent contains thiol groups to endcap the propagating polymer chains (FIG. 3A). The carboxylic acid terminal group can react with dopamine hydrochloride to introduce catechol groups to each polymer chain. The polymer chain terminal modification can have higher controllability with less variation of total catechol group amount in the final polymer product.

Example 4

Modification of PEO-PPO-PEO Triblock Copolymers

Figure 4A:
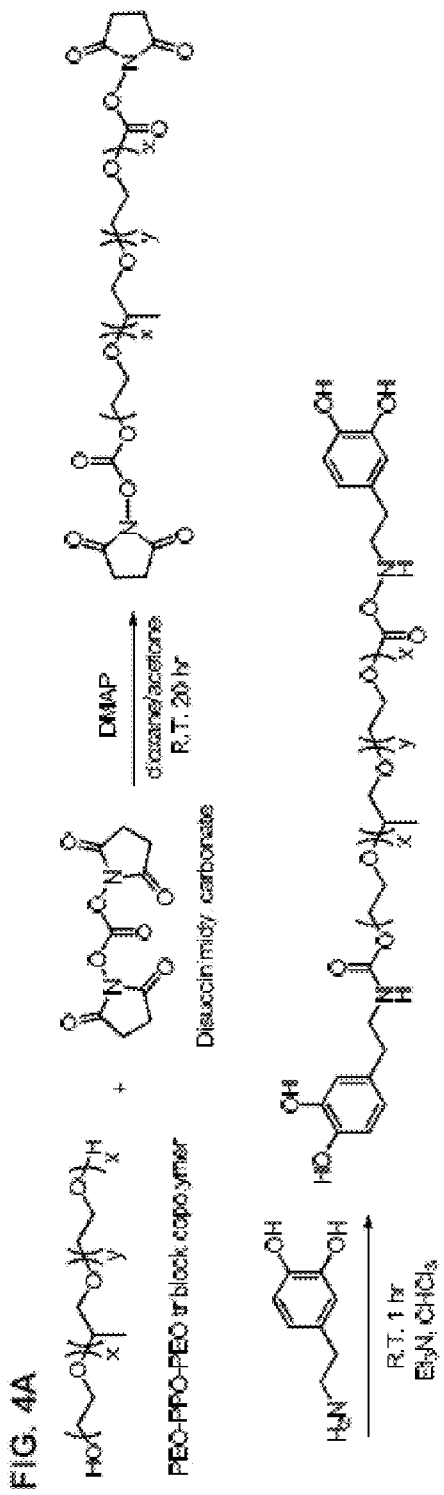
FIG. 4A and FIG. 4B show two schemes for functionalizing PEO-PPO-PEO triblock copolymers to have MDOPA endgroups.
Figure 4B:
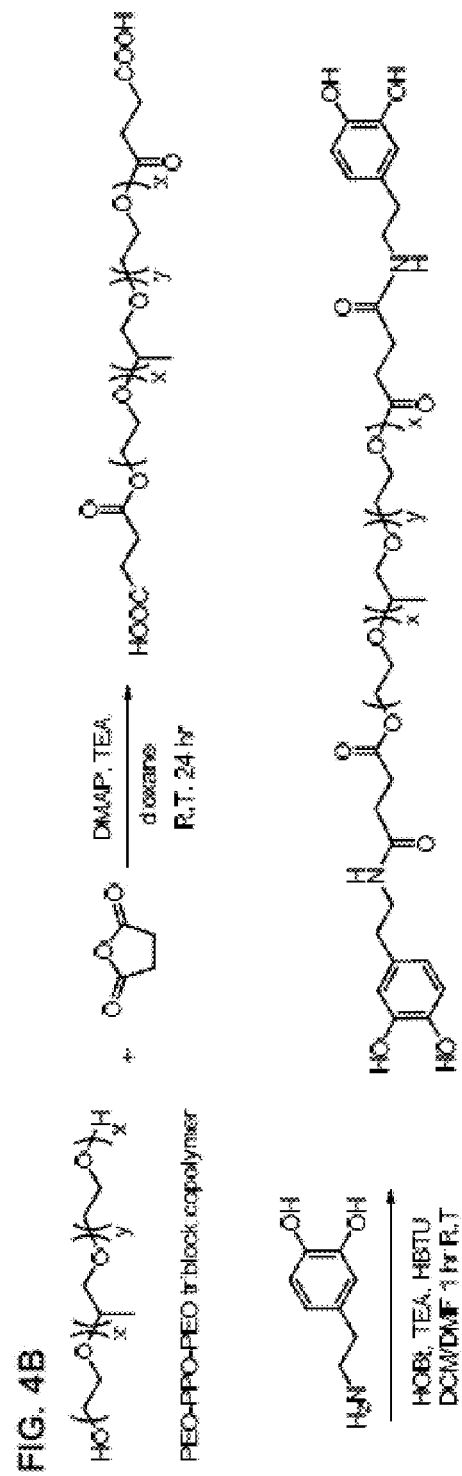

PEO-PPO-PEO triblock copolymer is another temperature sensitive polymers demonstrating LCST behavior. In particular, the low price and chemical stability of PEO-PPO-PEO triblock copolymer can be very competitive compare to other previously discussed temperature sensitive polymers. FIG. 4 shows terminal group modification of PEO-PPO-PEO triblock copolymers, wherein the terminal hydroxyl groups are shown to be converted to catechol groups. The overall amount of catechol chain terminal groups in the PEO-PPO-PEO triblock copolymer is small. Therefore, the adhesion property is not too strong to damage the cornea.

Example 5

LCST Tests of Prepared NIPAM-Based Polymers

In actual tests, pure water dissolved PNIPAM showed a very slow response on human palm due to slow diffusion of heat within the highly concentrated polymer solution. High concentration of PNIPAM in water is desirable because excessive water in the PNIPAM solution inhibits effective particle binding as the PNIPAM is heated. Therefore lower LCST material was needed to see fast response in high concentration of polymer. Additionally, because the ocular surface is exposed to the air to the, applied PNIPAM could be effected by external temperature, which is generally much lower than body temperature. So lower LCST than homo PNIPAM in pure water is an essential property for the eye-related applications of this invention.

Figure 5A:
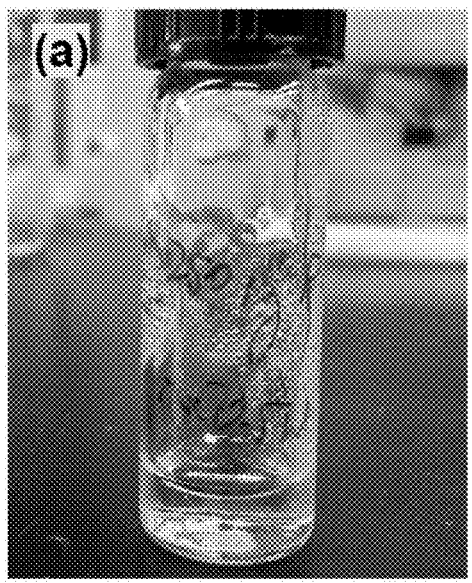
FIGS. 5A-C shows state changes of poly-NIPAM (PNIPAM; Mn: 44,000 g/mol) solution in 2.5% NaCl, concentration of polymer: 500 mg/mL of PNIPAM solution at room temperature (FIG. 5A); PNIPAM solution on human palm, No extra heating was applied (FIG. 5B); and broken pieces of solidified PNIPAM solution on human palm due to lack of toughness in solidified polymers (FIG. 5C)
Figure 5B:
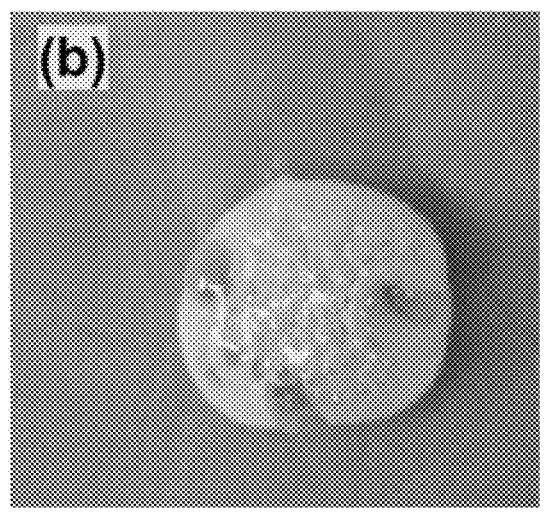

In general, LCST of NIPAM-based polymer solutions can be and was tested using UV-vis spectroscopy by monitoring the change of light intensity. The polymer solution becomes turbid with poor light transmittance above LCST. For the specific biomedical applications, the prepared NIPAM-based polymer solutions were tested on human palm to estimate LCST instead of using UV-vis in the present report. Typical examples of LCST test is shown in FIG. 5 and FIG. 6. Solid NIPAM-based polymers were homogeneously dissolved in designated amount of water or aqueous NaCl solution as shown in figure FIG. 5A. The dissolving process took a long time in general, as much as 48 hours in case of 166 mg/ml in 2.5% NaCl aqueous solution. As shown in FIGS. 6B and 6C, transparent NIPAM-based polymer solution turned to white solid when the solution was heated body temperature.

The data in Table 1 demonstrates the effects of NaCl concentration on LCST. PNIPAM solution in water shows LCST 32° C. according to a report in the literature. In higher concentration of NaCl in water, PNIPAM precipitated at lower temperature. The more NaCl in the water the lower LCST was observed. This phenomena is known as a specific ion effect, or Hofmeister effect. 2.5% NaCl in water was the optimal LCST for a given PNIPAM (number weight ($M_n$): 44,000 g/mole) solution. 0.9% NaCl did not show any change of LCST. PNIPAM solution took a long time to change its state to white solid under external heating supplier (moderate heating with hair dryer). 5% or above NaCl concentration showed too low LCST which is lower than room temperature (23° C.).

Figure 5C:
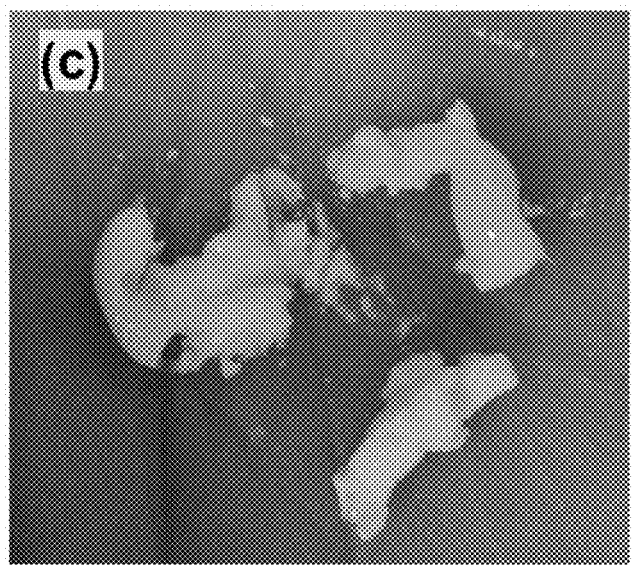
Figure 6A:
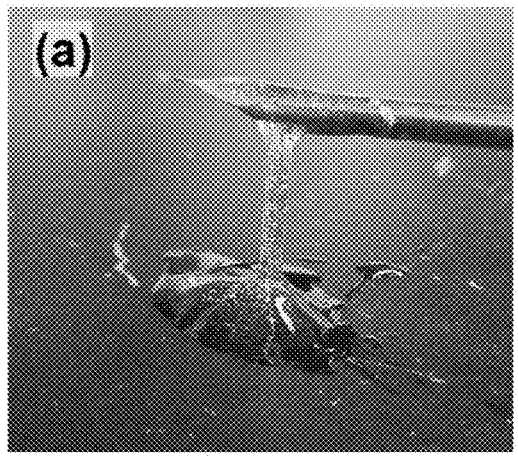
FIGS. 6A-C shows state changes of poly(NIPAM-co-MDOPA) ($M_n$: 150,000 g/mole) solution in 2.5% NaCl, concentration of copolymer: 166 mg/ml of copolymer solution at room temperature (FIG. 6A); the copolymer solution is sticky and viscous for effective capturing of particles on eyes; of rapidly solidified copolymer solution on human palm (FIG. 6B)
Figure 6B:
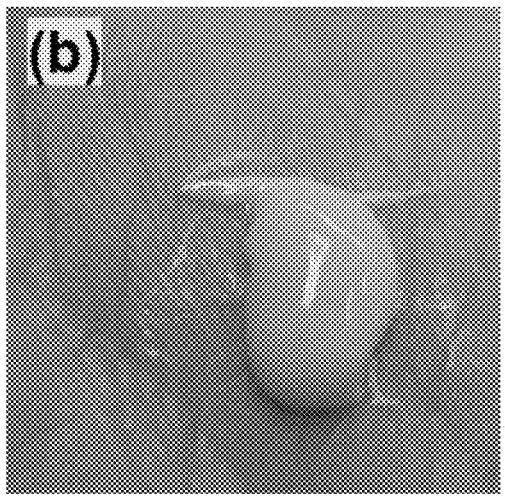
Figure 6C:
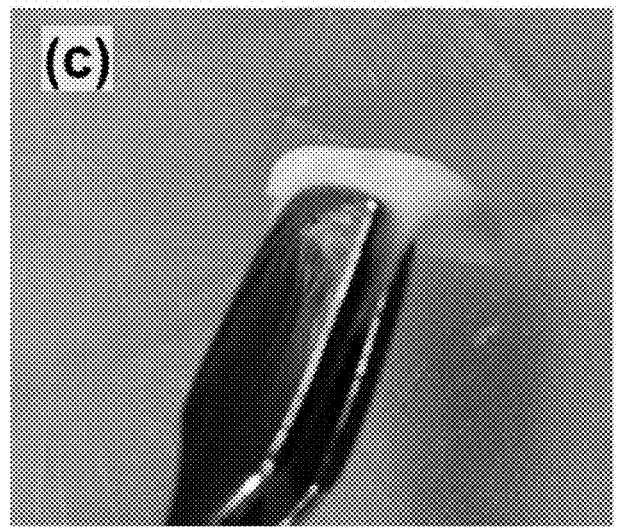

In spite of its optimal LCST, commercial PNIPAM, which had $M_n$ of 44,000 g/mole, showed weak and brittle properties after solidification at body temperature as shown in FIG. 5C. The formed NIPAM solid should be sufficiently robust and cohesive to allow for removal. High molecular weight polymer generates high entanglements of polymer chains, and consequently it enhances mechanical properties (toughness) of the polymer. Therefore, high $M_n$ PNIPAM and poly (NIPAM-co-MDOPA) were prepared. Absolute molecular weights of polymers were characterized by tetrahydrofuran (THF) eluent gel permeation chromatography (GPC).

TABLE 1

Behavior of homo PNIPAM in aqueous NaCl solutions

| NaCl concentration in water (w/v) | PNIPAM Concentration | Response on palm | Mechanical Property |
|---|---|---|---|
| 25% | 500 mg/ml | — | PNIPAM was not soluble in the NaCl solution. |
| 10% | 500 mg/ml | — | PNIPAM was only soluble at 0° C. |
|  | 250 mg/ml |  | Solid at room temperature. |
| 5% | 250 mg/ml | — | PNIPAM was only soluble at 0° C. |
|  | 175 mg/ml |  | Solid at room temperature. |
| 2.5% | 500 mg/ml | Solidified immediately | Soft and not tough (weak and brittle) |
| 0.9% | 500 mg/ml | No LCST change | Additional heat is need to solidify the solution. |

PNIPAM: Aldrich Catalog # 724459 ($M_n$: 44,000 g/mole)

Example 6

Adhesion Properties and Mechanical/Viscoelastic Properties of NIPAM-Based Polymers High molecular weight PNIPAM and poly(NIPAM-co-MDOPA) were prepared by using a reduced amount of solvent. In radical initiated polymerization, viscosity of polymerization solution increase due to growth of propagating chain. The viscosity change was negligible when a large amount of solvent was used. But the viscosity of polymerization system increased significantly when a reduced amount of solvent was used. In higher viscosity, propagation of reactive chain continued but chain termination via coupling was significantly limited. Therefore, a large molecular weight of polymers can be produced in reduced amount of solvent without changing other polymerization conditions. Using this principle, various molecular weights of NIPAM-based polymers were prepared. As shown in Table 2, three different $M_n$ of homo PNIPAM polymers were prepared. The lowest molecular weight, 44,000 g/mole, presented not enough toughness/mechanical properties after solidification at body temperature. The formed solid polymer was weak and brittle as shown in FIG. 5C, and therefore the solid could not be easily removed as a cohesive sheet by the practitioner in clinical application. The highest molecular weight, 1,040,000 g/mole, was not soluble both in pure water and 2.5% NaCl aqueous solution.

$M_n$ of 160,000 g/mole was the most suitable molecular weight for the present desired purposes. The highest possible polymer concentration in water or NaCl solution was needed to minimize water releasing after the NIPAM-based polymer solidified at high temperature. Also, at high concentration, other benefits were as followings: the polymer solution can be more easily placed on target sites than low viscosity liquid. Too thin liquid may flow away before it solidifies on target area. Additionally, highly concentrated polymer solution usually had more adhesion to target tissues than a low viscosity solution. As shown in Table 2, 83 mg/ml and 166 mg/ml were tested to find an optimal polymer concentration.

As mentioned earlier, the LCST drops in the presence of salt (NaCl). The higher concentration of NaCl drops the more LCST of PNIPAM. NaCl concentration of 2.5% and 5% were examined as shown in table 2. 5% NaCl concentration decreased LCST of PNIPAM too much, so the polymer solution was not liquid at room temperature. Unlike 5%, 2.5% NaCl showed liquid state at room temperature for both polymer concentration 83 mg/ml and 166 mg/ml. Finally, it is revealed that 166 mg/ml polymer concentration in 2.5% NaCl aqueous solution demonstrated the most suitable viscoelastic and mechanical properties for the practical purposes. However, its adhesion property was not as good as poly(NIPAM-co-MDOPA) under the same condition.

TABLE 2

Adhesion/mechanical properties of homo PNIPAM solution

| $M_n$ of polymer (g/mole) | NaCl in water (w/v) | Polymer concentration | Observed properties |
|---|---|---|---|
| 1,040,000 | Pure water and 2.5% | — | Not soluble |
| 160,000 | 2.5% | 83 mg/ml | Poor adhesion of polymer solution, solidified polymer not tough enough and too much water after polymer solidification |
|  |  | 166 mg/ml | Decent viscoelastic and mechanical properties but not enough adhesion property |
|  | 5% | 166 mg/ml | Solid at room temperature |
| 44,000 | 2.5% | 500 mg/ml | Solidified polymer not tough enough |

Based on homo PNIPAM test results, it was found that $M_n$ near 160,000 g/mole is a suitable molecular weight range to get a desirable viscoelastic and mechanical properties of solution and solidified polymers. Thus, $M_n$ of 150,000 g/mole poly(NIPAM-co-MDOPA) was prepared via AIBN-initiated radical polymerization (FIG. 1B). Poly(NIPAM-co-MDOPA) was solid in 5% NaCl solution because of too low LCST. The polymer solution in 5% NaCl aqueous media was liquid state at 0° C. in ice bath, but this much too low LCST is not practically useful. In 2.5% NaCl aqueous solution, two different poly(NIPAM-co-MDOPA) concentrations were prepared: 83 mg/ml and 166 mg/ml. As shown in Table 3, 83 mg/ml was too low concentration to show desirable properties in adhesion property, solidified polymer's properties at high temperature. Polymer concentration of 166 mg/ml demonstrated the best viscoelastic, mechanical properties and adhesion properties. Compare to homo PNIPAM, poly(NIPAM-co-MDOPA) has much higher adhesion properties under the same test conditions due to the presence of DOPA functionality in polymer chemical structure.

TABLE 3

Adhesion/mechanical properties of poly(NIPAM-co-MDOPA) solution

| $M_n$ of polymer (g/mole) | NaCl in water (w/v) | Polymer concentration | Observed properties |
|---|---|---|---|
| 150,000 | 2.5% | 83 mg/ml | Poor adhesion of polymer solution, solidified polymer not tough enough and too much water after polymer solidification |
|  |  | 166 mg/ml | Best viscoelastic, mechanical property and adhesion property |
|  | 5% | 166 mg/ml | Solid at room temperature |

Example 7

Animal Tests

Animal tests of PNIPAM was performed on the rabbit eye. The rabbit was sacrificed immediately before testing. Therefore, slightly lower body temperature was expected on than ocular surface than in a live animals. The expected lower body temperature was compensated by moderate external heating via hair dryer. Test procedures are presented in FIGS. 3 and 4 with photos.

Figure 7A:
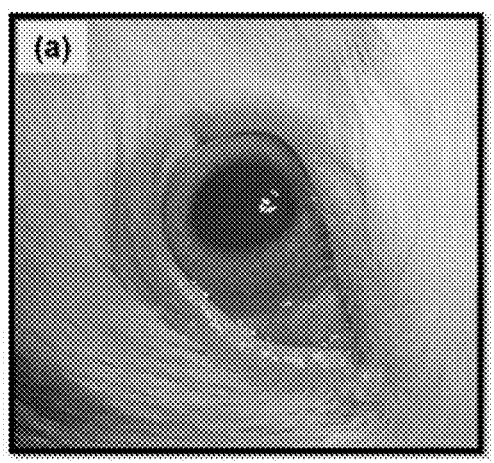
FIGS. 7A-H shows testing of removal of retained particles from ocular surface using homo PNIPAM ($M_n$: 44,000 g/mole) solution in pure water.
Figure 7B:
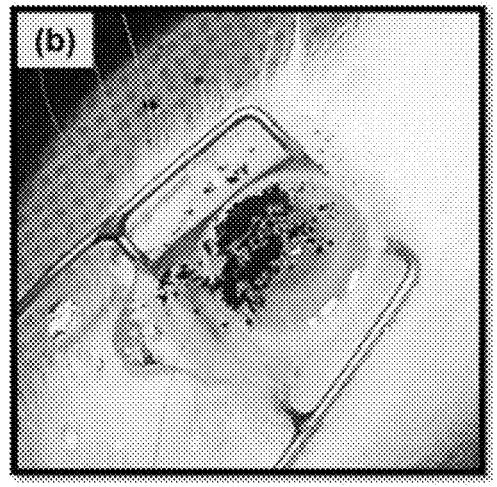
Figure 7C:
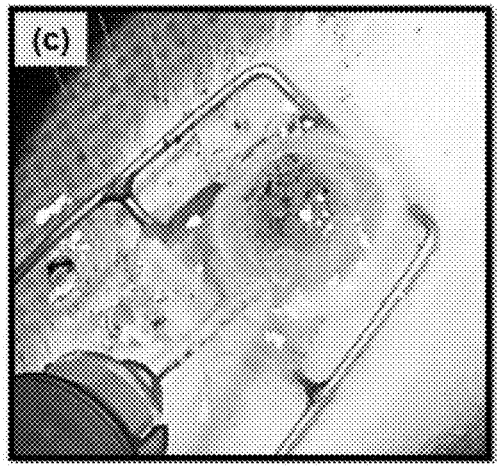
Figure 7D:
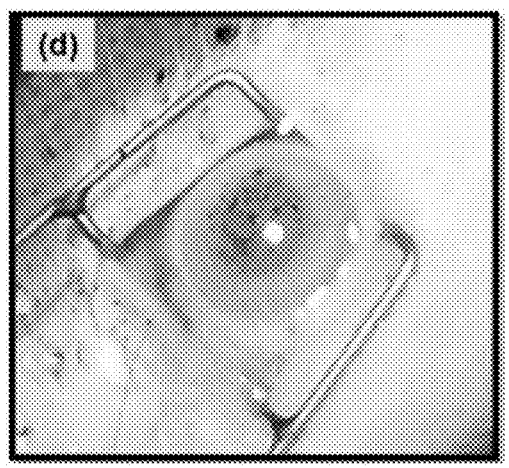
Figure 7E:
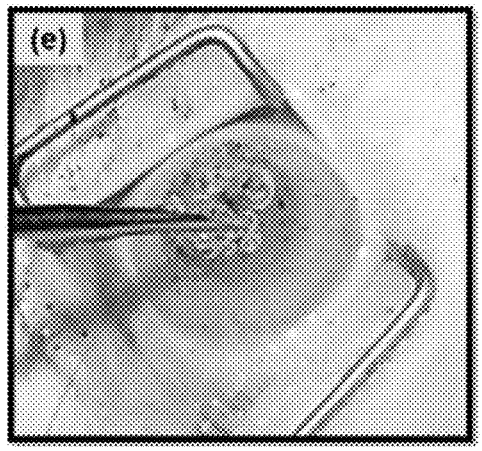
Figure 7F:
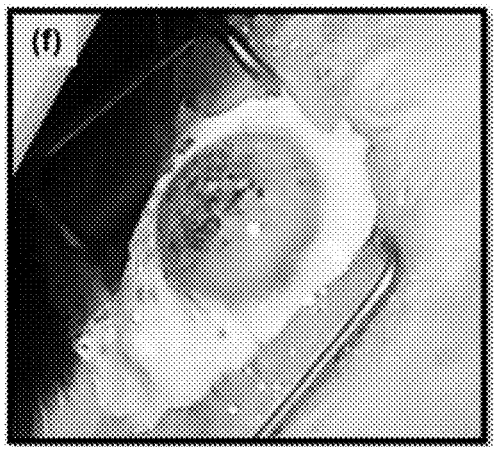
Figure 7G:
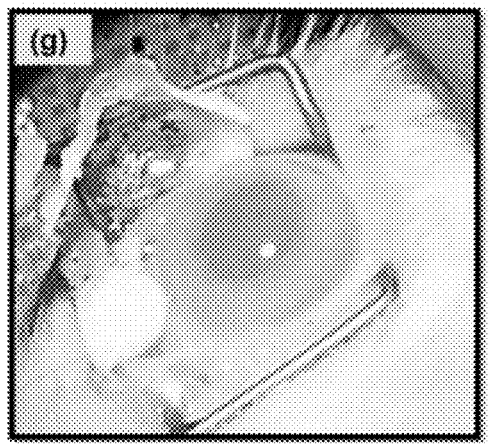
Figure 7H:
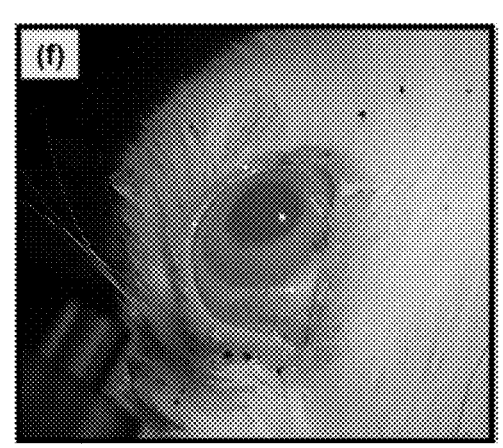

Ground charcoal power was used as a foreign particle for the animal tests. The charcoal powder was evenly scattered on rabbit's eye especially onto the corneal surface (FIG. 7B). The rabbit's eye was washed with physiological saline (0.9% NaCl) to remove the foreign material as shown in FIG. 7C. Despite vigorous irrigation, significant charcoal particles (charcoal powder) remained adherent to the ocular surface (FIG. 7D). PNIPAM solution ($M_n$ 44,000 g/mole and 500 mg/ml in pure water) was applied to the ocular surface (FIG. 4E). Following heating by the hair dryer, The PNIPAM solution became a white solid (FIG. 3f). The formed PNIPAM solid was then easily peeled from the rabbit's eye and the charcoal particles adhering to PNIPAM were removed as shown in FIG. 3(g). Thus, it is proven that applying temperature sensitive PNIPAM solution onto the ocular surface is an effective method to remove foreign particles (ground charcoal) that are removed by conventional saline irrigation. There was a concern of potential damage to the corneal epithelium caused by too strong an adhesion of the solid PNIPAM to the ocular surface. To test this, fluorescein sodium & benoxinate hydrochloride ophthalmic solution (Fluorescein) was applied to the rabbit eye after peeling off the PNIPAM. There was no evidence fluorescein staining indicating, indicating that application and peeling of the PNIPAM did not cause a corneal epithelial defect.

Figure 8A:
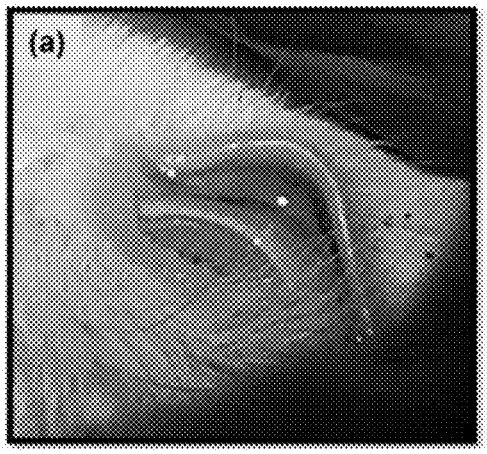
FIGS. 8A-E illustrates animal test procedure to remove particles from the underneath an eye lid (FIG. 8A); Black debris was remained under the eye lid even after the conventional saline washing (FIG. 8B); Placing of PNIPAM solution under the eye lid to adhere to remaining particles (FIG. 8C); Solidification: LCST behavior of NIPAM solution by body temperature and moderate hair dryer heating (FIG. 8D); Removal of solidified PNIPAM.
Figure 8B:
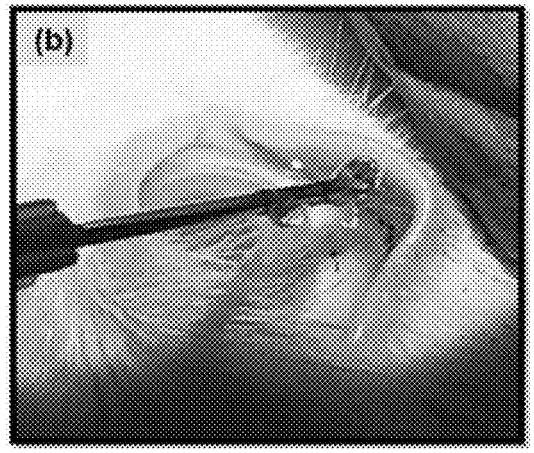
Figure 8C:
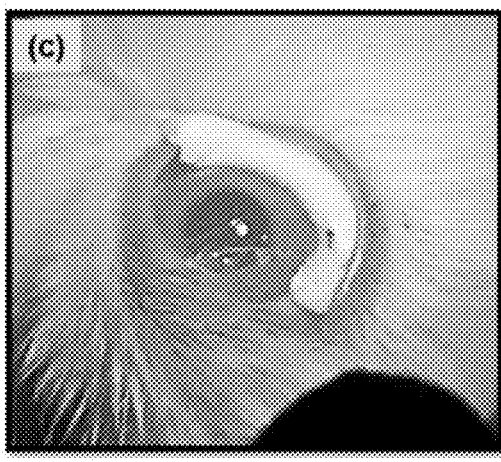
Figure 8D:
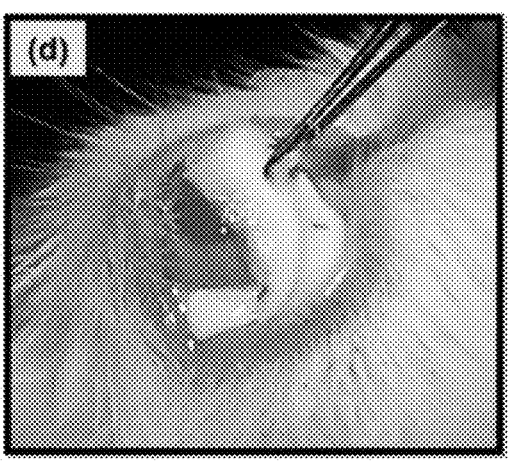
Figure 8E:
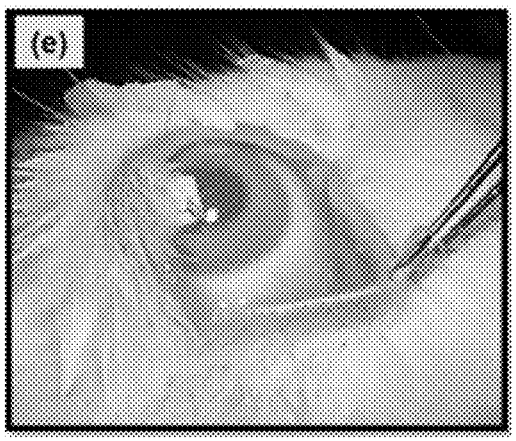

FIGS. 8A-E present another set of animal tests to remove foreign particles from underneath eye lid. Once foreign particle enter underneath eye lid and into the conjunctival fornix, it is difficult to remove these particles with further irrigation. FIG. 8A shows retention of charcoal particles in fornix and on palpebral conjunctiva despite vigorous saline irrigation. PNIPAM solution was applied to the ocular surface after retraction of the eyelid. (FIG. 8B). The PNIPAM solution turned to a white solid with moderate external heating as shown in FIG. 8C. The white PNIPAM solid with adherent charcoal particles was removed by forceps (FIG. 8D). Inspection of the inferior fornix showed no residual particles. (FIG. 8E).

The animal testing proved that PNIPAM solution is very promising material to remove foreign particles that cannot be removed by conventional irrigation. The PNIPAM solution was effective at removing particles from both the cornea as well as the palpebral conjunctiva and fornix. The homo PNIPAM solution revealed minor issues on animal tests: 1) because the formed solid was weak, removal process with forceps had to be performed very carefully by the practitioner 2) slightly higher adhesion is needed to effective removal of foreign particles 3) slightly low LCST is helpful to solidify NIPAM-based polymer solutions fast without external heating equipment. The listed three requirements can be satisfied by using above shown newly developed NIPAM-based polymer that is concentration of 166 mg/ml poly(NIPAM-co-MDOPA) solution in 2.5% NaCl containing aqueous media.

Example 8

Addition of Commercial Ocular Medicines to Prevent Possible Infections and/or to Facilitate Wound Healing Process Because chemical and non-chemical injuries to the eye are usually painful, an anesthetic can be added to the liquid polymer formulation. Similarly, in cases where there is concern for an associated infection as in penetrating ocular injuries, antibiotic can be added and the hardened polymer can be left on as a patch until medical attention is available. Other medicines applied to the ocular and other tissue surface can also be formulated into the polymer solution which can release them in a sustained fashion to underlying tissue(s).

Example 9

Exemplary Composition

An NIPAM-based polymer has been shown to be able to remove foreign particles, in a composition comprising poly(NIPAM-co-MDOPA) with a concentration of 166 mg/ml in 2.5% NaCl aqueous solution. Molecular weight of 150,000 g/mole for the NIPAM-based polymer showed desirable properties as a particle remover. The NIPAM segment contributed significantly to the LCST nature of poly(NIPAM-co-MDOPA). Low portion (5%) of MDOPA in poly(NIPAM-co-MDOPA) offered the effective wet adhesion property to capture foreign particle from the eye without damage to the ocular surface. The polymer's molecular weight 150,000 g/mole and concentration of 166 mg/ml helped maintain viscosity of solution for easy delivery via syringe/cannula and optimal adhesion properties. The presence of NaCl salt reduced the LCST of poly(NIPAM-co-MDOPA) solution to the appropriate temperature for use on external ocular tissues. The effectiveness of developed polymer was tested in a rabbit model and demonstrated excellent particle removal capability compared to the conventional saline washing method. The composition was compatible with additional medicines that can be added to formulation to confer anesthetic, analgesic, anti-infective and other desirable properties to these polymers in contact with ocular and non-ocular tissues.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. An aqueous composition comprising:
   (a) a copolymer comprising co-polymerized monomers of:
      (i) N-methacryloyl-3,4-dihydroxyl phenylalanine;
      (ii) N-isopropylacrylamide, N,N-dimethylacrylamide, N,N-diethylacrylamide, 2-aminoethyl methacrylate, 2-(dimethylamino)ethyl (meth)acrylate, 2-(dimethylamino)ethyl(meth)acrylamide, N-(3-aminopropyl)-(meth)acrylate, or a combination thereof; and
      (iii) optionally (meth)acrylic acid; or
   (b) a polymer or copolymer comprising co-polymerized monomers of N-isopropylacrylamide, N,N-dimethylacrylamide, N,N-diethylacrylamide or a combination thereof, the polymer or copolymer being end capped by at least one 4-(2-amino-ethyl)-benzene-1,2-diol group, each group linked to the polymer or copolymer by a 3-mercaptopropionic acid ester linkage; or
   (c) a PEO-PPO-PEO copolymer, PEO-PPO copolymer, PPO-PEO-PPO copolymer, or a mixture thereof, end capped by at least one 4-(2-amino-ethyl)-benzene-1,2-diol, each group linked to the copolymer by a carbamate or an ethylene 1,2-dicarboxyester linkage;
   wherein the N-methacryloyl-3,4-dihydroxyl phenylalanine or 4-(2-amino-ethylbenzene-1,2-diol is present in a range of about 0.1 mol % to about 10 mol %, based on the total monomer content of the copolymer;
   the copolymer has a number average, Mn, molecular weight in a range of from about 50,000 to about 500,000 g/mol and is present in the composition in a range of about 10 mg/mL to about 500 mg/mL of the composition;
   said composition having a lower critical solubility temperature (LCST) in a range of from about 15° C. to about 35° C.

2. The composition of claim 1, the composition having a lower critical solubility temperature (LCST) of less than 32° C.

3. The composition of claim 1, wherein the copolymer comprises co-polymerized monomers of N-methacryloyl-3,4-dihydroxyl phenylalanine and at least one of N-isopropylacrylamide, N,N-dimethylacrylamide, N,N-diethylacrylamide, 2-aminoethyl methacrylate, 2-(dimethylamino)ethyl (meth)acrylate, 2-(dimethylamino)ethyl(meth)acrylamide, or N-(3-aminopropyl)-(meth)acrylate.

4. The composition of claim 1, wherein the 3,4-dihydroxyphenyl alanine is 3,4-dihydroxy-L-phenyl alanine.

5. The composition of claim 1, wherein the 3,4-dihydroxyphenyl alanine is present in the copolymer in a range of about 1 to about 10 mol %, based on the total monomer composition of the copolymer.

6. The composition of claim 1, wherein the copolymer comprises copolymerized monomers of N-methacryloyl03,4-dihydroxyl phenylalanine and N-isopropylacrylamide (NIPAM).

7. The composition of claim 1, wherein the copolymer concentration is in a range of about 50 mg/mL to about 250 mg/mL of total composition.

8. The composition of claim 4, wherein the 3,4-dihydroxy-L-phenyl alanine being is arranged in at least one block polymer segment in the copolymer.

9. The composition of claim 4, wherein the 3,4-dihydroxy-L-phenyl alanine being is randomly distributed throughout the copolymer.

10. The composition of claim 1, wherein the copolymer was prepared by free radical polymerization, ring opening metathesis polymerization (ROMP), atom transfer radical polymerization (ATRP), nitroxide mediate polymerization (NMP), or reverse addition-fragmentation chain transfer polymerization (RAFT) of the respective monomers.

11. The composition of claim 1, further comprising sodium chloride present in a concentration range of about 1 wt % to about 5 wt %, relative to the weight of the composition.

12. The composition of claim 1, further comprising a topical anesthetic.

13. The composition of claim 1, further comprising an antibiotic, anti-viral, or antifungal medicament.

14. The composition of claim 1, further comprising an ophthalmic dye.

15. The composition of claim 1, the composition being acceptable for human use.

16. The composition of claim 1, comprising:
   (a) a copolymer comprising co-polymerized monomers of:
      (i) N-methacryloyl-3,4-dihydroxyl phenylalanine;
      (ii) N-isopropylacrylamide, N,N-dimethylacrylamide, N,N-diethylacrylamide, 2-aminoethyl methacrylate, 2-(dimethylamino)ethyl (meth)acrylate, 2-(dimethylamino)ethyl(meth)acrylamide, N-(3-aminopropyl)-(meth)acrylate, or a combination thereof; and
      (iii) optionally (meth)acrylic acid; wherein:
   the composition has a lower critical solubility temperature (LCST) of in a range of from about 30° C. to about 34° C.;
   the 3,4-dihydroxyphenyl alanine monomer units incorporated in the copolymer are present in the copolymer in a range of about 3 to about 6 mol %%, based on the total monomer content of the copolymer;
   the copolymer has a number average, $M_n$, molecular weight in a range of from about 100,000 to about 200,000 g/mol and is present in the composition in a range of about 50 mg/mL to about 250 mg/mL of the composition;
   the composition comprises sodium chloride in a concentration range of about 1 wt % to about 5 wt %, relative to the weight of the composition; and one or more of
   (a) a topical anesthetic;
   (b) an antibiotic, anti-viral, or antifungal medicament;
   (c) or an ophthalmic dye; and
   the composition is acceptable for human use.

17. A method of removing particles from a tissue surface of a mammalian patient, said method comprising:
   (a) applying an aqueous composition of claim 1 onto the tissue surface, said tissue surface contaminated with at least one foreign particle; and
   (b) waiting sufficient time for the temperature of the composition to equilibrate to the temperature of the tissue surface, optionally applying heat to the aqueous composition while on the tissue surface, such that the copolymer precipitates from the composition onto the tissue surface, and adheres to the at least one foreign particle.

18. The method of claim 17 further comprising (c) removing the precipitated copolymer and the at least one adhered foreign particle from the tissue surface.

19. A method of removing particles from an ocular surface of an eye of a human patient, said method comprising:
   (a) applying an aqueous composition of claim 16 onto the ocular surface of a human patient, said ocular surface contaminated with at least one foreign particle, said aqueous composition being applied at a temperature less than the lower critical solubility temperature (LCST) of the aqueous composition;

(b) waiting sufficient time for the temperature of the composition to equilibrate to the temperature of the ocular surface, optionally applying heat to the aqueous composition while on the ocular surface of the patient, such that the copolymer precipitates from the composition onto the ocular surface.

20. The method of claim 19, further comprising (c) removing the precipitated copolymer and the adhered foreign particle(s) from the ocular surface.

21. A method of protecting an eye of a patient, said method comprising:

(a) applying an aqueous composition of claim 1 onto the ocular surface of a patient, said aqueous composition being applied at a temperature less than the lower critical solubility temperature (LCST) of the aqueous composition; and (b) waiting sufficient time for the temperature of the composition to equilibrate to the temperature of the eye, optionally applying heat to the aqueous composition while on the eye of the patient, such that the copolymer precipitates from the composition onto the ocular surface.

* * * * *